(12) United States Patent
De Pater

(10) Patent No.: US 8,951,958 B2
(45) Date of Patent: Feb. 10, 2015

(54) PURIFICATION OF CASPOFUNGIN INTERMEDIATES

(75) Inventor: Robertus Mattheus De Pater, Delft (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 13/637,386

(22) PCT Filed: Mar. 22, 2011

(86) PCT No.: PCT/EP2011/054351
§ 371 (c)(1),
(2), (4) Date: Sep. 26, 2012

(87) PCT Pub. No.: WO2011/120842
PCT Pub. Date: Oct. 6, 2011

(65) Prior Publication Data
US 2013/0018171 A1    Jan. 17, 2013

(30) Foreign Application Priority Data

Mar. 29, 2010   (EP) ................. 10158204

(51) Int. Cl.
| | | |
|---|---|---|
| A61K 38/08 | (2006.01) | |
| A61K 38/12 | (2006.01) | |
| A61P 31/10 | (2006.01) | |
| C07K 1/14 | (2006.01) | |
| C07K 1/16 | (2006.01) | |
| C07K 7/54 | (2006.01) | |
| C07K 7/50 | (2006.01) | |
| C07K 7/00 | (2006.01) | |
| C07K 7/56 | (2006.01) | |

(52) U.S. Cl.
CPC ...................... C07K 7/56 (2013.01)
USPC ............ 514/1.1; 514/2.3; 514/3.6; 514/3.3; 530/317; 530/329; 530/344

(58) Field of Classification Search
CPC ....... A61K 38/00; A61K 38/04; A61K 38/08; A61K 38/12; A61K 38/005; C07K 7/50; C07K 7/54; C07K 7/56; C07K 1/20; C07K 1/22; C07K 1/00; C07K 1/14; C07K 1/16
See application file for complete search history.

(56) References Cited

U.S. PATENT DOCUMENTS

2009/0291996 A1*   11/2009   Korodi et al. ............ 514/410

FOREIGN PATENT DOCUMENTS

| WO | WO 02/083713 | 10/2002 |
| WO | WO 2009/142761 | 11/2009 |
| WO | WO 2009/158034 | 12/2009 |

OTHER PUBLICATIONS

Schwartz et al., Journal of Antibiotics (1992) 45, 1853-1866.*
International Search Report for PCT/EP2011/054351, mailed Apr. 14, 2011.
Leonard et al., "Synthesis of the antifungal [beta]-1, 3-glucan synthase inhibitor CANCIDAS (caspofungin acetate) from pneumocandin B0", *Journal of Organic Chemistry*, American Chemical Society, vol. 72, No. 7, Mar. 30, 2007, pp. 2335-2343.

* cited by examiner

*Primary Examiner* — Karlheinz R Skowronek
*Assistant Examiner* — Catherine Mader
(74) *Attorney, Agent, or Firm* — Nixon & Vanderhye P.C.

(57) ABSTRACT

The present invention relates to a method for the purification of cyclopeptides of general formula (3) by means of a silicate.

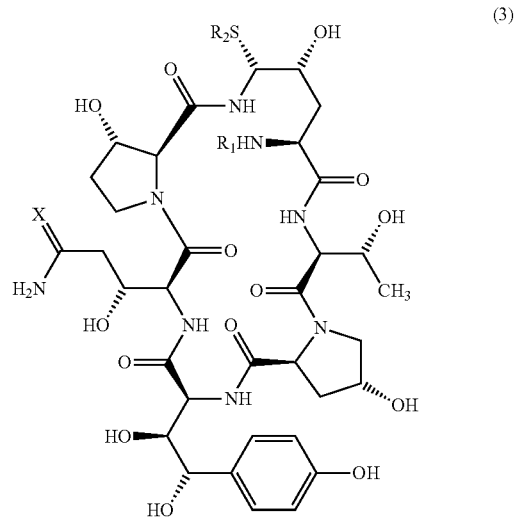

(3)

8 Claims, 2 Drawing Sheets

PURIFICATION OF CASPOFUNGIN INTERMEDIATES

Figure 1:
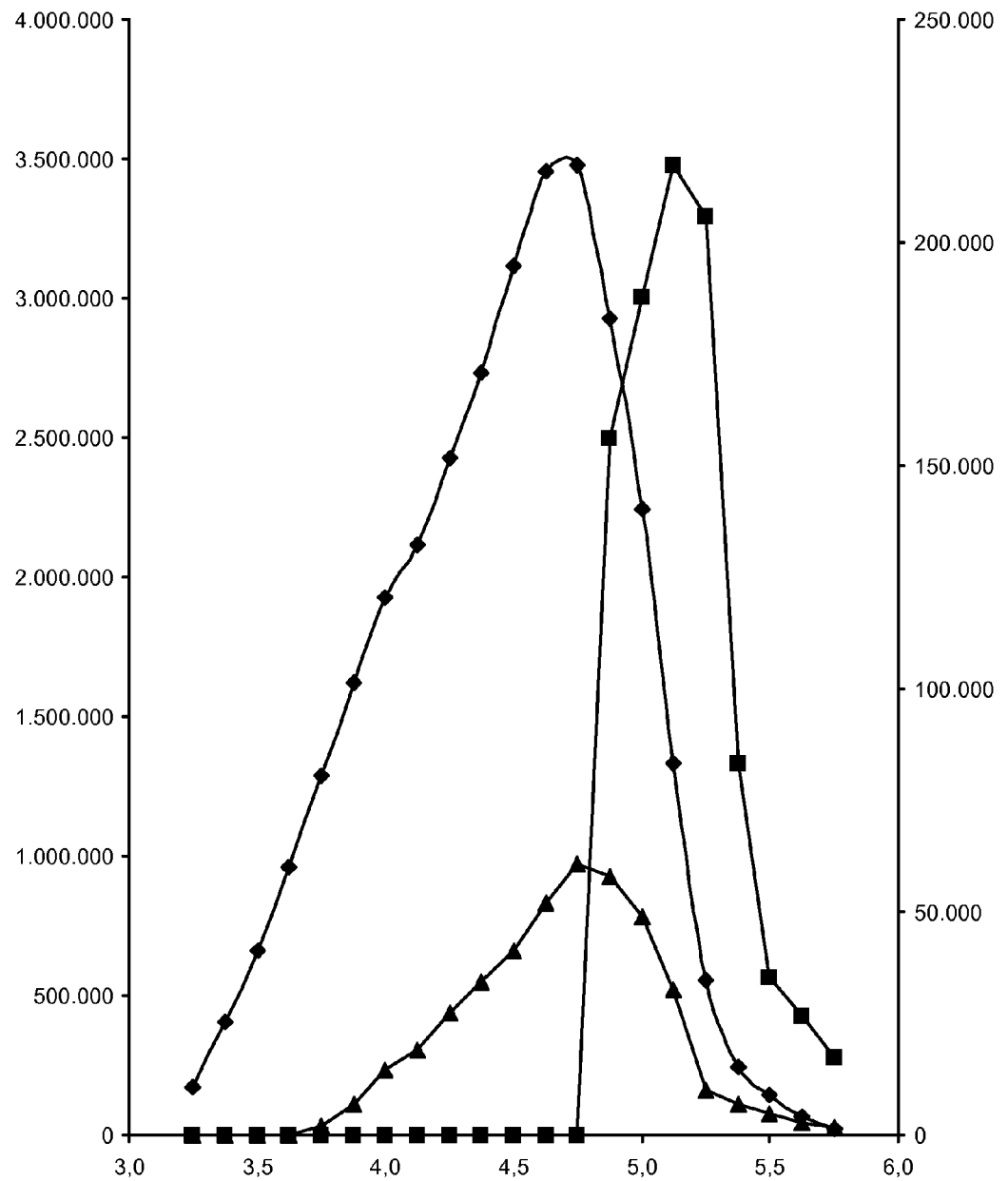

This application is the U.S. national phase of International Application No. PCT/EP2011/054351 filed 22 Mar. 2011 which designated the U.S. and claims priority to EP Patent Application No. 10158204.7 filed Mar. 29, 2010, the entire contents of each of which are hereby incorporated by reference.

FIELD OF THE INVENTION

The present invention relates to a method for the purification of cyclopeptides.

BACKGROUND OF THE INVENTION

Cyclopeptides are polypeptides in which the terminal amine and carboxyl groups form an internal peptide bond. Several cyclopeptides are known for their advantageous medicinal properties. An excellent example of this is the class of echinocandins which are potent antifungals. Cyclopeptides can be naturally occurring compounds but may also be obtained by total synthesis or by synthetic or genetic modification of naturally occurring or naturally produced precursors; the latter class is referred to as semi synthetic cyclopeptides. Examples of medicinally useful echinocandins are the cyclic hexapeptides anidulafungin, caspofungin, cilofungin and micafungin which are useful in treating fungal infections especially those caused by *Aspergillus, Blastomyces, Candida, Coccidioides* and *Histoplasma*. Anidulafungin, caspofungin and micafungin are all semi synthetic cyclopeptides derivable from naturally occurring echinocandins such as for instance echinocandin B, pneumocandin $A_0$ or pneumocandin $B_0$.

Although nature can provide a substantive part of the complex chemical structure of semi synthetic cyclopeptides, and in many cases having all chiral centers in the required configuration, a major disadvantage nevertheless is that during fermentation often side products are formed that carry through the process and eventually end up as impurities. Only in few cases can fermentation processes be tuned in such a way as to prevent formation of impurities. Particularly when these impurities are structurally closely related to the main product, their removal is usually tedious and often requires unprecedented purification approaches as the main products in question are chemically unstable and/or prone to racemization.

The preparation of caspofungin (1) from fermentatively obtained pneumocandin $B_0$ (2) (with $R_1$=C(O)(CH$_2$)$_8$CH(CH$_3$)CH$_2$CH(CH$_3$)CH$_2$CH$_3$) in both compounds), is a process wherein removal of impurities is an important issue.

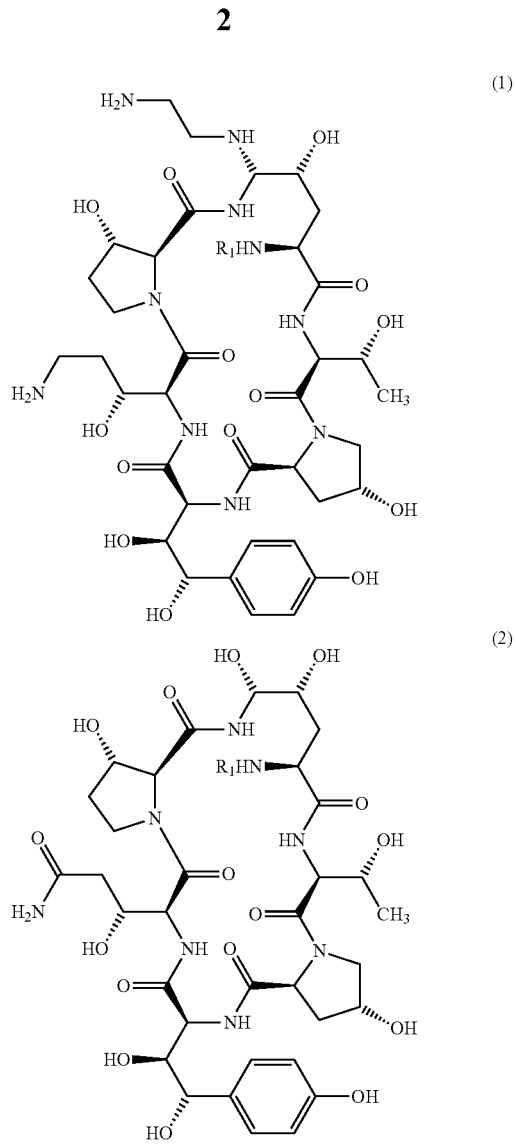

A multitude of structurally related impurities occurring during fermentation of pneumocandin $B_0$ (2, $R_1$=C(O)(CH$_2$)$_8$CH(CH$_3$)CH$_2$CH(CH$_3$)CH$_2$CH$_3$)) has been described. Examples are compounds having an additional methyl function (such as pneumocandin $A_0$, pneumocandin $A_1$, pneumocandin $A_2$, pneumocandin $A_3$, pneumocandin $A_4$, pneumocandin $A_5$, pneumocandin $A_6$), compounds lacking one or two hydroxyl groups (such as pneumocandin $B_1$, pneumocandin $B_2$, pneumocandin $B_5$, pneumocandin $B_6$, pneumocandin $E_0$), compounds having a 4-hydroxy proline rather than a 3-hydroxy proline moiety (pneumocandin $C_0$), compounds having additional hydroxyl groups (such as pneumocandin $D_0$, pneumocandin $D_2$) or the recently described impurity A (US 2009/0324635) wherein, in the caspofungin structure, one of the hydroxy-L-ornithine moieties is replaced by an L-serine moiety.

Minimizing the $C_0$ impurity (i.e. the pneumocandin/caspofungin cyclopeptide structure having a 4-hydroxy proline rather than a 3-hydroxy proline moiety), is the subject of US 2009/0291996 advocating to purify the starting material of the pneumocandin $B_0$ to caspofungin conversion. Thus, crude pneumocandin $B_0$ (2) (with $R_1$=C(O)(CH$_2$)$_8$CH(CH$_3$)CH$_2$CH(CH$_3$)CH$_2$CH$_3$) is purified by chromatography followed by crystallization from a solvent-antisolvent mixture. Given the very high similarity between desired structure and impurity, not only in terms of the many different chemical reactive sites present in both molecules, but also in terms of charge, hydrophilicity and molecular weight, such a successful separation is not normally expected for other, similar, molecules and seems an unexpected result and for the skilled person probably limited to the substrates as disclosed in US 2009/0291996.

Removal of impurities that are structurally closely related but are electronically markedly different from pneumocandin is an object yet to be realized. For example, molecules bearing an alkyl- or arylthio functionality rather than a hydroxyl group are electronically different from the pneumocandin core structure. Such differences are expected to lead to quite differing behavior in chromatographic procedures

DETAILED DESCRIPTION OF THE INVENTION

Removal of impurities that are structurally closely related to the pneumocandin/caspofungin core structure was surprisingly achieved with intermediates that are obtained in the pneumocandin $B_0$ to caspofungin conversion.

In a first aspect of the present invention there is provided a method for the purification of a compound of general formula (3)

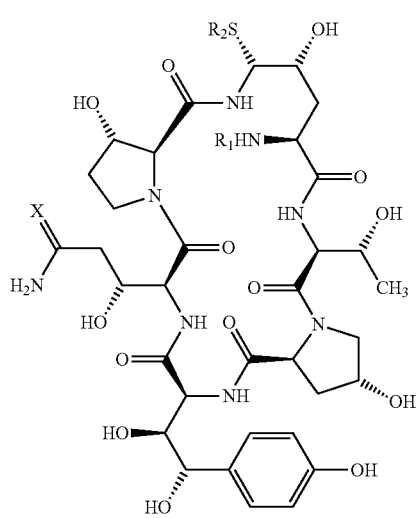

(3)

wherein $R_1$ is C(O)$R_3$ with $R_3$ is $C_9$-$C_{21}$ alkyl, $C_9$-$C_{21}$ alkenyl, $C_1$-$C_{10}$ alkoxyphenyl, $C_1$-$C_{10}$ alkoxynaphthyl or $C_1$-$C_{10}$ alkoxyterphenyl and wherein $R_2$ is benzimidazol-2-yl, benzothiazol-2-yl, 1-methylimidazol-2-yl, 4-methoxyphenyl or phenyl and wherein X is O or H,H, comprising the steps of:
  (a) dissolving a compound of general formula (3) as defined above in a first solvent;
  (b) contacting the solution obtained in step (a) with silica gel;
  (c) eluting said compound of general formula (3) with a second solvent As compared to pneumocandin $B_0$, the purification of which is described in US 2009/0291996, the compounds of the first aspect of the present invention are characterized in quite different chemical behavior caused by the introduction of a thio-functionality instead of a hydroxyl group. Still further away from the pneumocandin core are those molecules wherein also an amide functionality (X=O) is replaced with an amine group (X=H, H). These differences as compared to pneumocandin $B_0$, will lead to differences in charge, hydrophilicity and molecular weight. Since any or all of these characteristics play a pivotal role in successful separation of the $C_0$ impurity from pneumocandin $B_0$, it is to be expected that major changes in the substrates will disturb the separation behavior.

Nevertheless, it was found that in compound (3), with $R_1$ is C(O)$R_3$ with $R_3$ is $C_9$-$C_{21}$ alkyl, $C_9$-$C_{21}$ alkenyl, $C_1$-$C_{10}$ alkoxyphenyl, $C_1$-$C_{10}$ alkoxynaphthyl or $C_1$-$C_{10}$ alkoxyterphenyl and with $R_2$ is benzimidazol-2-yl, benzothiazol-2-yl, 1-methylimidazol-2-yl, 4-methoxyphenyl or phenyl, a successful separation of the $C_0$ impurity (i.e. compound (5) with $R_1$ and $R_2$ as described above) could be achieved using a silicate in the case wherein X is O. This appeared particularly functional for the caspofungin core wherein $R_1$ is C(O)(CH$_2$)$_8$CH(CH$_3$)CH$_2$CH(CH$_3$)CH$_2$CH$_3$. Preferably group $R_2$ is phenyl and preferably the silicate is silica gel. Preferably a solution of crude compound (3) as defined above is brought into contact with a silicate. After a period of time sufficient for allowing adsorption, the liquid phase is separated from the silicate. Appropriate periods of time are from 1 min to 24 h, preferably from 5 min to 12 h. Removal of the liquid phase can be achieved using various techniques such as filtration, centrifugation, evaporation and the like. Suitable solvent are any solvents in which the substrate dissolves with a preference for alcohols such as for example ethanol and methanol. Elution from the silicate can be effected by applying solvents or solvent mixtures. Preferably a solvent mixture is applied comprising an alcohol, an ester and water.

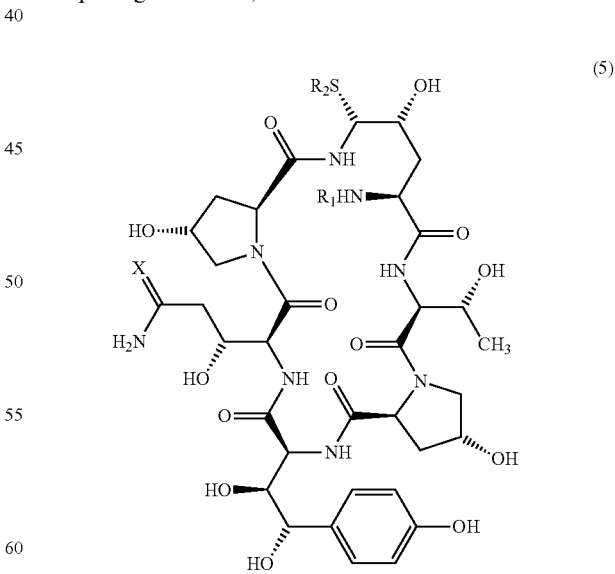

(5)

In a first embodiment the mixture of silicate and crude compound (3) obtained above is applied to a column of silicate prior to elution with solvent or solvent mixture. It was found that this increases separation between the various components, notably compounds (3) and (5)

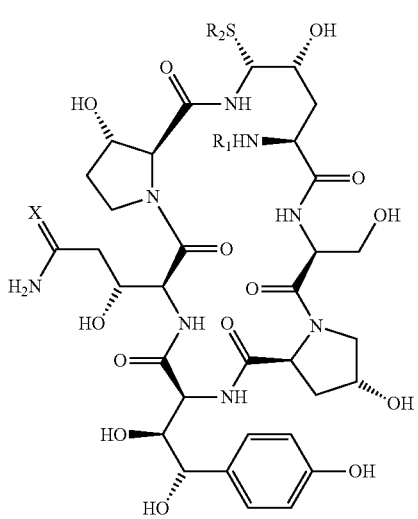
(4)

Still more surprisingly, in a second embodiment it was found that in compound (3), with $R_1$ and $R_2$ as defined above but with X is H,H (prepared as described for instance in J. Org. Chem. 2007, 72, 2335-2343), not only a successful separation of the $C_0$ impurity could be achieved, but also another impurity that is notoriously difficult to remove, could be separated. The impurity in question is the so-called impurity A of general formula (4) with $R_1$, $R_2$ and X as defined above, reported in J. Ind. Microbiol. Biotechnol. 2001, 26, 216-221. In US 2009/0324635, removal of impurity A was reported using reversed phase chromatography of the crude end product, caspofungin. Clearly the simultaneous purification of the second embodiment offers advantages as it circumvents an additional step and may be performed at an early step in the synthesis process. The solvents or solvent mixtures used in the second embodiment may be the same as mentioned in the first embodiment. Preferably, a solvent mixture is used comprising an acid, for example from 0.1 to 10%, preferably from 0.2 to 5%, most preferably from 0.5 to 2% (v/v). Suitable acids are small molecular weight acids such as hydrochloric acid, sulfuric acid, formic acid and the like. A preferred acid is acetic acid.

In a second aspect of the present invention there is provided a composition comprising a compound of general formula (3), from 0.0001% to 0.2% by weight of a compound of general formula (4) and/or from 0.0001% to 0.2% by weight of a compound of general formula (5), wherein $R_1$ is $C(O)R_3$ with $R_3$ is $C_9$-$C_{21}$ alkyl, $C_9$-$C_{21}$ alkenyl, $C_1$-$C_{10}$ alkoxyphenyl, $C_1$-$C_{10}$ alkoxynaphthyl or $C_1$-$C_{10}$ alkoxyterphenyl and wherein $R_2$ is benzimidazol-2-yl, benzothiazol-2-yl, 1-methylimidazol-2-yl, 4-methoxyphenyl or phenyl and wherein X is O or H,H. Preferably $R_1$ is $C(O)(CH_2)_8CH(CH_3)CH_2CH(CH_3)CH_2CH_3$ and/or $R_2$ is phenyl.

LEGEND TO THE FIGURES

FIG. 1 is the UPLC analysis of the purification of compound (3) with $R_1$ is $C(O)(CH_2)_8CH(CH_3)CH_2CH(CH_3)CH_2CH_3$, $R_2$ is phenyl and X is oxygen on silica gel 60 using ethyl acetate/methanol/water (85/9/6, v/v/v) as eluting solvent. X-axis: column fractions in bed volumes (bed volume is 100 mL and fractions of ⅛ bed volume were analyzed). Left Y-axis: measured peak area for compound (3; ♦). Right Y-axis: measured peak area for compounds (4; ▲) and (5; ■) with $R_1$, $R_2$ and X as defined above.

Figure 2:
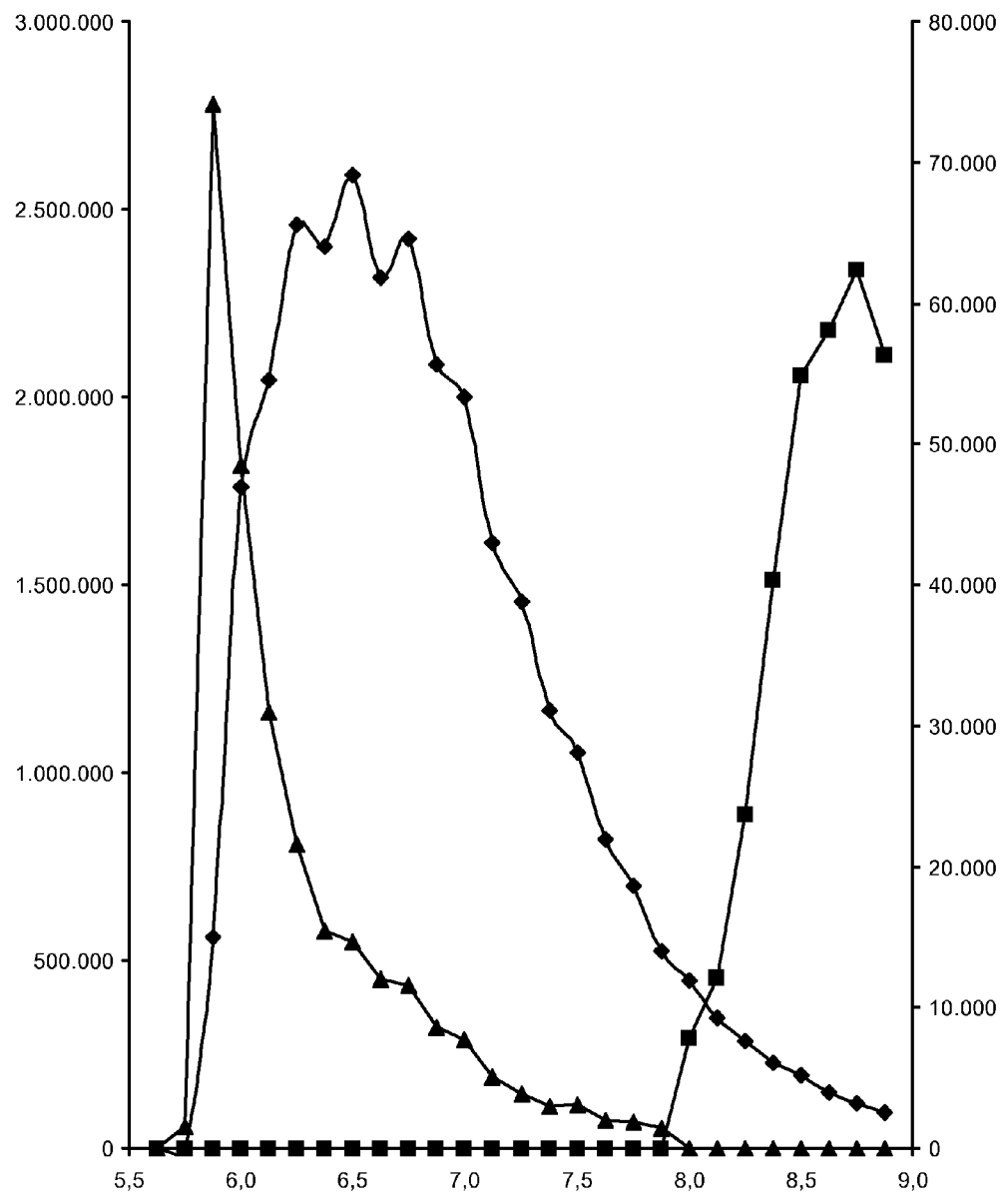

FIG. 2 is the UPLC analysis of the purification of compound (3) with $R_1$ is $C(O)(CH_2)_8CH(CH_3)CH_2CH(CH_3)CH_2CH_3$, $R_2$ is phenyl and X is H,H on silica gel 60 using ethyl acetate/methanol/water/acetic acid (76/17/7/1, v/v/v/v) as eluting solvent. X-axis: column fractions in bed volumes (bed volume is 100 mL and fractions of ⅛ bed volume were analyzed). Left Y-axis: measured peak area for compound (3; ♦). Right Y-axis: measured peak area for compounds (4; ▲) and (5; ■) with $R_1$, $R_2$ and X as defined above.

EXAMPLES

General

Pneumocandin $B_0$ was obtained by fermentation of *Glarea Lozoyensis* (*Zalerion arboricola*) as described in WO 2000/008197. Commercially available reagents were used as received unless mentioned otherwise. Solvents were dried over 3 Å molecular sieves. UPLC analysis was carried out using an Acquity UPLC BEH C18 1.7 μm (2.1*150 mm) column (Art nr 186002353) under the following conditions:
Injection volume: 2 μL
Flow: 0.35 mL·min$^{-1}$
Column temp: 60° C.
Mobile phase A: 50 mM phosphate buffer pH 6.0
Mobile phase B: 75% acetonitrile
Injection mode: Full loop
Gradient:

| Time (min) | Flow | % A | % B |
|---|---|---|---|
| Initial | 0.35 | 33 | 67 |
| 25 | 0.35 | 33 | 67 |
| 35 | 0.35 | 0 | 100 |
| 40 | 0.35 | 0 | 100 |
| 45 | 0.35 | 33 | 67 |
| 50 | 0.35 | 33 | 67 |

Example 1

Preparation and Purification of Thiophenyl-Substituted Pneumocandin $B_0$ (3; $R_1$=C(O)(CH$_2$)$_8$CH(CH$_3$)CH$_2$CH(CH$_3$)CH$_2$CH$_3$; $R_2$=phenyl; X=O)

In the below experimental description, all compounds mentioned have $R_1$, $R_2$ and X as defined in the title.

Under nitrogen finely divided pneumocandin $B_0$ (0.68 g, assay total pneumocandins 95%, assay pneumocandin ($B_0$ and $C_0$) 81%; 0.61 mmol pneumocandins) and cyclohexylboronic acid (156 mg, 1.22 mmol) were added to acetonitrile (20 mL, pre-dried on molecular sieves of 3 Å). To this suspension thiophenol (190 μL, 1.86 mmol) was added. The suspension was cooled and maintained at −15° C. and trifluoromethanesulfonic acid (163 μL, 1.83 mmol) was added and the reaction mixture was maintained at −15° C. for 20 h under nitrogen. The conversion was followed by HPLC: sample after 3 h (50 μL reaction mixture+20 μL 0.85 M sodium acetate+0.88 mL methanol): conversion was 79%; after 20 h the conversion was 97%. The reaction mixture was quenched with 0.844 M sodium acetate trihydrate (2.2 mL; 1.86 mmol). The suspension was warmed to 17° C., maintained for 2 h, and cooled to 0° C. and stirred at 0° C. overnight, during which the concentration of the title compound in the mother-liquor decreased from 2.1 to 1.6 g·L$^{-1}$. The precipitate was filtered off, washed with 90% acetonitrile (3×10 mL), and dried under vacuum at 30° C., giving 0.53 g of crude compound (3) as an off-white powder with an HPLC-assay of 87%. The isolated yield was 77%.

Crude compound (3) (300 mg) containing 3% of compound (5) was dissolved in 1.8 mL methanol. Silica gel 60 (15-40 μm; 1.5 g) was added and the mixture was dried under vacuum overnight at 20° C., giving a dry mix of (3) and silica gel. A column with an internal diameter of 2 cm was filled with 50 g silica gel 60 (15-40 μm) in a mixture of ethyl acetate/methanol/water=85/9/6 (v/v/v), giving a bed height of 33 cm (bed-volume of 100 mL). The dry mix of (3) and silica gel was loaded on top of the column and the column was eluted with ethyl acetate/methanol/water=85/9/6 (v/v/v) at ~1 bar with a flow of 64 min per bed volume. Fractions of 12.5 mL were collected and analyzed with UPLC. The results are given in the below Table.

|   | A | B | C | D | E | F | G (3) | H (5)/(3) | I (3) | J (3) | K (5) | L (5) |
|---|---|---|---|---|---|---|---|---|---|---|---|---|
|   | Bed volume | (3) (area) | (4) (area) | (5) (area) | (4)/(3) (%) | (5)/(3) (%) | Yield cum (%) | Cum (%) | Purity (%) | Purity Cum (%) | Purity (%) | Purity Cum (%) |
| 1 | 3.25 | 171269 | 0 | 0 |  | 0 | 0.54 | 0 | 100.0 | 100.0 | 0.0 |  |
| 2 | 3.375 | 404972 | 0 | 0 |  | 0 | 1.8 | 0 | 100.0 | 100.0 | 0.0 |  |
| 3 | 3.5 | 660080 | 0 | 0 |  | 0 | 3.9 | 0 | 100.0 | 100.0 | 0.0 |  |
| 4 | 3.625 | 959459 | 0 | 0 |  | 0 | 6.9 | 0 | 100.0 | 100.0 | 0.0 |  |
| 5 | 3.75 | 1291663 | 2039 | 0 | 0.16 | 0 | 10.9 | 0 | 99.8 | 99.9 | 0.0 |  |
| 6 | 3.875 | 1619905 | 7035 | 0 | 0.43 | 0 | 16 | 0 | 99.6 | 99.8 | 0.0 |  |
| 7 | 4 | 1930374 | 14648 | 0 | 0.76 | 0 | 22.1 | 0 | 99.2 | 99.7 | 0.0 |  |
| 8 | 4.125 | 2115259 | 18976 | 0 | 0.9 | 0 | 28.7 | 0 | 99.1 | 99.5 | 0.0 |  |
| 9 | 4.25 | 2429948 | 27445 | 0 | 1.13 | 0 | 36.3 | 0 | 98.9 | 99.4 | 0.0 |  |
| 10 | 4.375 | 2732147 | 34220 | 0 | 1.25 | 0 | 44.9 | 0 | 98.8 | 99.3 | 0.0 |  |
| 11 | 4.5 | 3119040 | 41283 | 0 | 1.32 | 0 | 54.6 | 0 | 98.7 | 99.2 | 0.0 |  |
| 12 | 4.625 | 3454291 | 51935 | 0 | 1.5 | 0 | 65.5 | 0 | 98.5 | 99.1 | 0.0 |  |
| 13 | 4.75 | 3479442 | 60844 | 0 | 1.75 | 0 | 76.4 | 0 | 98.3 | 99.0 | 0.0 |  |
| 14 | 4.875 | 2928032 | 58028 | 156132 | 1.98 | 5.3 | 85.5 | 0.57 | 93.2 | 98.3 | 5.0 | 5.0 |
| 15 | 5 | 2242754 | 48923 | 187782 | 2.18 | 8.4 | 92.6 | 1.16 | 90.5 | 97.7 | 7.6 | 6.1 |
| 16 | 5.125 | 1331942 | 32481 | 217270 | 2.44 | 16.3 | 96.7 | 1.82 | 84.2 | 97.0 | 13.7 | 7.8 |
| 17 | 5.25 | 558307 | 10073 | 205982 | 1.8 | 36.9 | 98.5 | 2.44 | 72.1 | 96.4 | 26.6 | 9.6 |
| 18 | 5.375 | 246866 | 7064 | 83362 | 2.86 | 33.8 | 99.3 | 2.69 | 73.2 | 96.2 | 24.7 | 10.2 |
| 19 | 5.5 | 145992 | 4877 | 35314 | 3.34 | 24.2 | 99.7 | 2.78 | 78.4 | 96.1 | 19.0 | 10.4 |
| 20 | 5.625 | 67959 | 2789 | 26817 | 4.1 | 39.5 | 99.9 | 2.86 | 69.7 | 96.0 | 27.5 | 10.6 |
| 21 | 5.75 | 22761 | 1905 | 17425 | 8.37 | 76.6 | 100 | 2.91 | 54.1 | 95.9 | 41.4 | 10.8 |

Example 2

Purification of Compound (3; $R_1$=C(O)(CH$_2$)$_8$CH(CH$_3$)CH$_2$CH(CH$_3$)CH$_2$CH$_3$; $R_2$=phenyl; X=H,H)

In the below experimental description, all compounds mentioned have $R_1$, $R_2$ and X as defined in the title.

|   | A | B | C | D | E | F | G (3) | H (5)/(3) | I (3) | J (3) | K (5) | L (5) |
|---|---|---|---|---|---|---|---|---|---|---|---|---|
|   | Bed volume | (3) (area) | (4) (area) | (5) (area) | (4)/(3) (%) | (5)/(3) (%) | Yield cum (%) | Cum (%) | Purity (%) | Purity Cum (%) | Purity (%) | Purity Cum (%) |
| 1 | 5.625 | 0 | 0 | 0 |  | 0 | 0 | 0 |  |  |  |  |
| 2 | 5.75 | 1900 | 1500 | 0 | 78.95 | 0 | 0 | 0 | 55.9 | 55.9 | 0.0 |  |
| 3 | 5.875 | 560284 | 74180 | 0 | 13.46 | 0 | 1.9 | 0 | 88.3 | 88.1 | 0.0 |  |
| 4 | 6 | 1758759 | 48507 | 0 | 5.35 | 0 | 7.8 | 0 | 97.3 | 94.9 | 0.0 |  |
| 5 | 6.125 | 2047428 | 30912 | 0 | 3.55 | 0 | 14.6 | 0 | 98.5 | 96.6 | 0.0 |  |
| 6 | 6.25 | 2460372 | 21572 | 0 | 2.59 | 0 | 22.9 | 0 | 99.1 | 97.5 | 0.0 |  |
| 7 | 6.375 | 2399033 | 15398 | 0 | 2.08 | 0 | 30.9 | 0 | 99.4 | 98.0 | 0.0 |  |
| 8 | 6.5 | 2589642 | 14678 | 0 | 1.75 | 0 | 39.6 | 0 | 99.4 | 98.3 | 0.0 |  |
| 9 | 6.625 | 2318404 | 11991 | 0 | 1.55 | 0 | 47.4 | 0 | 99.5 | 98.5 | 0.0 |  |
| 10 | 6.75 | 2421938 | 11532 | 0 | 1.39 | 0 | 55.5 | 0 | 99.5 | 98.6 | 0.0 |  |
| 11 | 6.875 | 2085308 | 8580 | 0 | 1.28 | 0 | 62.5 | 0 | 99.6 | 98.7 | 0.0 |  |
| 12 | 7 | 1998696 | 7717 | 0 | 1.19 | 0 | 69.2 | 0 | 99.6 | 98.8 | 0.0 |  |
| 13 | 7.125 | 1609967 | 5102 | 0 | 1.13 | 0 | 74.6 | 0 | 99.7 | 98.9 | 0.0 |  |
| 14 | 7.25 | 1454946 | 3859 | 0 | 1.08 | 0 | 79.5 | 0 | 99.7 | 98.9 | 0.0 |  |
| 15 | 7.375 | 1165706 | 2967 | 0 | 1.04 | 0 | 83.4 | 0 | 99.7 | 99.0 | 0.0 |  |
| 16 | 7.5 | 1051984 | 3040 | 0 | 1.01 | 0 | 86.9 | 0 | 99.7 | 99.0 | 0.0 |  |
| 17 | 7.625 | 824130 | 2037 | 0 | 0.99 | 0 | 89.7 | 0 | 99.8 | 99.0 | 0.0 |  |
| 18 | 7.75 | 700253 | 1853 | 0 | 0.97 | 0 | 92 | 0 | 99.7 | 99.0 | 0.0 |  |
| 19 | 7.875 | 523113 | 1379 | 0 | 0.95 | 0 | 93.8 | 0 | 99.7 | 99.1 | 0.0 |  |
| 20 | 8 | 445958 | 0 | 7812 | 0.94 | 1.8 | 95.2 | 0.03 | 98.3 | 99.0 | 1.7 | 1.7 |
| 21 | 8.125 | 346115 | 0 | 12132 | 0.93 | 3.5 | 96.4 | 0.07 | 96.6 | 99.0 | 3.4 | 2.5 |
|   | 8.25 | 286249 | 0 | 23667 | 0.92 | 8.3 | 97.4 | 0.15 | 92.4 | 98.9 | 7.6 | 3.9 |
|   | 8.375 | 226478 | 0 | 40281 | 0.91 | 17.8 | 98.1 | 0.29 | 84.9 | 98.8 | 15.1 | 6.0 |
|   | 8.5 | 193583 | 0 | 54884 | 0.91 | 28.4 | 98.8 | 0.47 | 77.9 | 98.6 | 22.1 | 8.5 |

-continued

| A | B | C | D | E | F | G | H | I | J | K | L |
|---|---|---|---|---|---|---|---|---|---|---|---|
| Bed volume | (3) (area) | (4) (area) | (5) (area) | (4)/(3) (%) | (5)/(3) (%) | (3) Yield cum (%) | (5)/(3) Cum (%) | (3) Purity (%) | (3) Purity Cum (%) | (5) Purity (%) | (5) Purity Cum (%) |
| 8.625 | 147629 | 0 | 58063 | 0.9 | 39.3 | 99.3 | 0.66 | 71.8 | 98.5 | 28.2 | 10.7 |
| 8.75 | 121872 | 0 | 62403 | 0.9 | 51.2 | 99.7 | 0.87 | 66.1 | 98.3 | 33.9 | 12.8 |
| 8.875 | 95516 | 0 | 56271 | 0.89 | 58.9 | 100 | 1.06 | 62.9 | 98.1 | 37.1 | 14.5 |

Crude compound (3) (300 mg) containing 1% of compound (4) and 3% of compound (5) was dissolved in 2 mL methanol. Silica gel 60 (15-40 µm; 1.5 g) was added and the mixture was dried under vacuum overnight at 20° C., giving a dry mix of (3) and silica gel. A column with an internal diameter of 2 cm was filled with 50 g silica gel 60 (15-40 µm) in a mixture of ethyl acetate/methanol/water/acetic acid=76/17/7/1 (v/v/v/v), giving a bed height of 33 cm (bed-volume of 100 mL). The dry mix of (3) and silica gel was loaded on top of the column and the column was eluted with ethyl acetate/methanol/water/acetic acid=76/17/7/1 (v/v/v/v) at ~1 bar with a flow of 64 min per bed volume. Fractions of 12.5 mL were collected and analyzed with UPLC. The results are given in the above Table.

The invention claimed is:

1. A method for the purification of a compound of general formula (3):

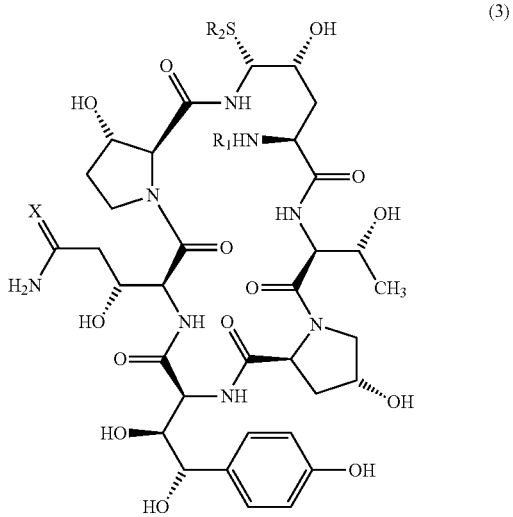

(3)

wherein $R_1$ is $C(O)R_3$ with $R_3$ is $C_9$-$C_{21}$ alkyl, $C_9$-$C_{21}$ alkenyl, $C_1$-$C_{10}$ alkoxyphenyl, $C_1$-$C_{10}$ alkoxynaphthyl or $C_1$-$C_{10}$ alkoxyterphenyl and wherein $R_2$ is benzimidazol-2-yl, benzothiazol-2-yl, 1-methylimidazol-2-yl, 4-methoxyphenyl or phenyl and wherein X is O or H,H, comprising the steps of:

(a) dissolving a compound of general formula (3) as defined above in a first solvent;

(b) contacting the solution obtained in step (a) with silica gel; and (c) eluting the compound of general formula (3) at a purity of 98.3% or greater with a second solvent.

2. The method according to claim 1, wherein said first solvent is removed prior to performing step (c).

3. The method according to claim 1, further comprising isolating the compound of general formula (3) after step (c).

4. The method according to claim 1, wherein said first solvent is an alcohol.

5. The method according to claim 1, wherein said second solvent comprises an ester, an alcohol and water.

6. The method according to claim 5, wherein said second solvent further comprises an acid.

7. The method according to claim 1, wherein $R_1$ is $C(O)(CH_2)_8CH(CH_3)CH_2CH(CH_3)CH_2CH_3$.

8. The method according to claim 7, further comprising converting the compound of general formula (3) into caspofungin or a pharmaceutically acceptable salt thereof.

* * * * *